United States Patent [19]

Glen R. Harding

[11] Patent Number: 4,949,731

[45] Date of Patent: Aug. 21, 1990

[54] ORAL PROPHYLACTICS

[76] Inventor: Glen R. Harding, 656 Rosemont, La Jolla, Calif. 92037

[21] Appl. No.: 89,780

[22] Filed: Aug. 27, 1987

[51] Int. Cl.$^5$ ............................................. A61F 6/00
[52] U.S. Cl. .................................... 128/842; 128/857; 128/859; 128/844; 128/918
[58] Field of Search .................... 128/136, 132 R, 156, 128/201.15, 203.11, 205.17, 202.28, 206.14, 842, 843, 844, 859, 918, 330; 604/347-353

[56] References Cited

U.S. PATENT DOCUMENTS

| | | | |
|---|---|---|---|
| D. 246,117 | 10/1977 | Okamoto | 128/844 |
| D. 246,119 | 10/1977 | Okamoto | 128/844 |
| 1,365,684 | 1/1921 | Guise | 128/860 |
| 1,986,988 | 1/1935 | Treadwell | 128/857 |
| 2,606,324 | 8/1952 | Mafko | 2/206 |
| 2,667,869 | 2/1954 | D'elia | 128/132 R |
| 4,004,591 | 1/1977 | Freimark | 604/330 |
| 4,050,457 | 9/1977 | Davidson | 128/202.28 |
| 4,320,752 | 3/1982 | Comparetto | 128/844 |
| 4,415,548 | 11/1983 | Reddy | 128/844 |
| 4,544,357 | 10/1985 | Williams | 433/136 |
| 4,583,946 | 4/1986 | Shanel | 433/136 |
| 4,600,387 | 7/1986 | Ross | 433/136 |

FOREIGN PATENT DOCUMENTS 210413 5/1908 Fed. Rep. of Germany.
05291 7/1988 World Int. Prop. O..

OTHER PUBLICATIONS

Bech, Claus; Kama Sutra, 1984; p. 87.
ALT for damerne; Jun. 30, 1988; p. 68.
S. Zussman, "Sex & Health", Glamour, Sep. 1987.
Terry E. Johnson, "An Unflinching Aids Compaign", 05/25/87, Newsweek.
Allan Parachini, "Condom Standards Face Revisons", 9/23/87, LA Times.
Abigail Van Buren, "Dear Abby,", 10/18/87, LA Times "Collectors Gold Edition," Lawrence Research Group.

Primary Examiner—Robert A. Hafer
Assistant Examiner—Michael Brown

[57] ABSTRACT

An elastic and flexible oral prophylactic that conforms to the mouth. The hygienic appliance may incorporate texture and flavor, and includes impermeable and permeable embodiments.

9 Claims, 3 Drawing Sheets

ORAL PROPHYLACTICS

FIELD OF THE INVENTION

This invention relates generally to the field of hygienic appliances, and more particularly to prophylactic devices.

A problem that has become important because of its immediate and devastating consequences is sexually transmitted diseases. Condoms are related to the present invention; they are effective prophylactics against sexual diseases. In view of the fact that fluids are passed via oral intercourse it should therefore be evident that a new device that provides prophylaxis for oral intercourse would constitute a significant improvement over the state of the art. The immediate prophylaxis the device provides is particularly suited, for example, to individuals that otherwise suffer by oral paths of venereal or other distressing diseases.

In view of the foregoing factors and conditions characteristic of the prior art, it is a primary objective of the present invention to provide a novel appliance that helps reduce the incidents of diseases, especially via oral intercourse.

Another objective of the present invention is to provide a hygienic appliance that is worn for the mouth that is easily applied and removed and is shaped for the lips, tongue, and mouth and is comfortable to wear.

Still another objective of the present invention is to provide a relatively simple and inexpensive hygienic appliance that is worn for the mouth that allows for a maximum of tactile sensation.

A further objective of the present invention is to provide a hygienic appliance that may incorporate colors, textures, and flavors.

Still a further objective of the present invention is to provide effective and comfortable means of holding the device in place for the mouth.

And still a further objective of the present invention is to provide a hygienic appliance that is permeable.

And yet still a further objective of the present invention is to provide a hygienic appliance that allows the comfortable swallowing and maintenance of the user's own saliva.

SUMMARY

The oral prophylactic includes a resilient, elastic and flexible body construction having a thin-walled portion to be received into the mouth over the tongue of a wearer, and further having a labial portion that fits about the lips of the wearer.

DRAWINGS

DESCRIPTION

Figure 1:
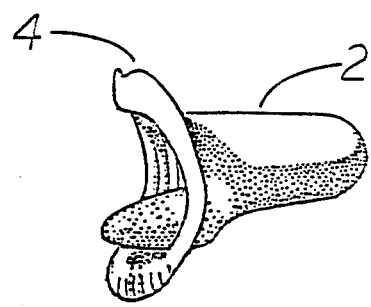
FIG. 1 is a side view of an embodiment of the device showing an elongated portion 2 and a lips portion 4.
Figure 2:
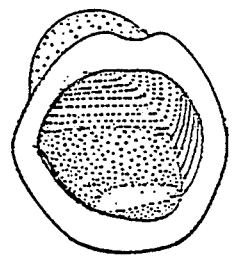
FIG. 2 is a frontal view of an embodiment of the device.

According to a preferred embodiment of the present invention, the hygienic appliance includes a resilient and flexible unitary body construction having a tubular portion received into the mouth, and also integrally having a labial portion that fits over the lips. Referring now to the drawings and particularly FIG. 1, a hygienic appliance is shown with an elongated tubular portion 2, and a labial portion 4. The tubular portion 2 and the labial portion 4 are dimensioned to fit comfortably; both portions are also elastic and flexible enough to accommodate the natural range of movement of the lips, mouth, and tongue. The hygienic appliance may also be fabricated in several sizes and styles to accommodate the requirements of the purchasing public.

One preferred embodiment of the present invention is fabricated as a unitary construction in a process using well known rubber or synthetic flexible material. The tubular portion 2 is adapted to the natural shape of the mouth of simply bulbous shapes. The labial portion 4 is adapted to the natural shape of the lips or simply elliptical shapes.

Figure 3:
FIG. 3 shows another embodiment of the device textured on its inner and outer surfaces.
Figure 4:
FIG. 4 is a perspective view of an embodiment of the device being worn in the user's mouth.
Figure 5:
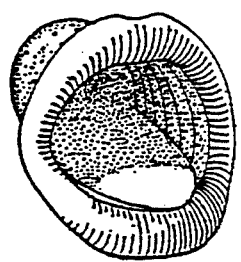
FIG. 5 is a perspective view of an embodiment of the device showing texture on the inner and outer surface.

In accordance with another embodiment of the invention, FIG. 3 shows that the inner and outer surfaces of the tubular portion 2 and the labial portion 4 may be textured to enhance their tactile use.

In accordance with yet another embodiment of the invention, the tubular portion 2 and the labial portion 4 may incorporate flavors.

Figure 6:
FIG. 6 shows yet another embodiment of the device where adhesive tabs are used to secure the device onto facial skin.
Figure 7:
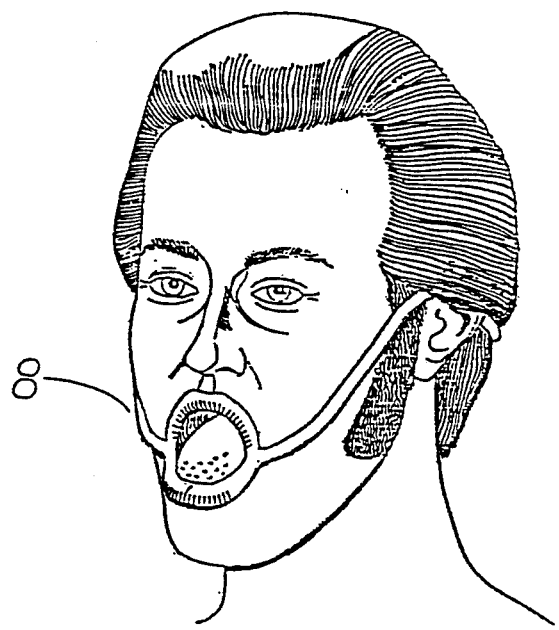
FIG. 7 illustrates an additional means of attaching the device to a user's face.

In accordance with still another embodiment of the invention, FIG. 6 shows that the device may be secured in place with adhesive tabs 6. The securing tabs 6 are integrally formed with the device and also have an adhesive method on their inner surface. In packaging the hygienic appliance the adhesive is protected, for example, by a peel-off type of paper.

It is to be pointed out that the materials herein specified are examples and any ones having desired characteristics may be substituted for those specifically identified. Although a limited number of embodiments of the invention have been described in some detail, it should be realized that modifications and other embodiments incorporating the inventive features may be constructed; those skilled in the art will envision that many other possible variations are within its scope. For example, skilled artisans will readily be able to change the dimensions and shapes of the various embodiments, and substitute alternative materials to make the oral prophylactic. Accordingly, it is intended that the foregoing disclosure and drawings shall be considered only as illustrations of the principles of the invention.

A purpose of the present invention is to provide a means of prophylaxis against diseases via oral intercourse.

In the embodiment depicted by FIG. 1, the tubular portion 2 is received into the mouth, and the labial portion 4 is set for the lips. The inner surface of the labial portion 4 may also have an adhesive for fastening onto skin peripheral to the outline of the lips.

In the embodiment depicted by FIG. 6, the integral tabs 6 function to secure the hygienic appliance in place by fastening to facial skin. The tabs are placed by first peeling away a protective paper on the inside surface of the tabs, and then pressing the adhesive surface onto facial skin.

The above specifics exemplify some embodiments of the present invention as its advantages relate to prophylaxis via oral intercourse; variations of and from this purpose are possible.

The hygienic appliance is potentially useful in other applications exploiting the adroitness of the tongue. A specific example is painting by handicapped individuals having no utility of their hands. Another barrier method example is an oral dam for dentistry.

The present invention serves as a barrier method and a prophylactic against diseases. The requirements for its design therefore inform a variety of fabrication materials. For example, materials that are permeable are particularly well-suited.

Although the present invention has been described with reference to certain preferred embodiments, other versions are possible. Therefore the spirit and scope of the appended claims should not be limited to description of the versions contained herein.

I claim:

1. An oral prophylactic for use in the mouth and adapted for the lips of a wearer comprising:
    an elastic unitary, liquid impermeable body having a thin-walled tubular portion received into the mouth over the tongue of the wearer, the tubular portion being closed at a first end located in the mouth of the wearer, and having an open end remote from said first end, said open end entirely surrounded by a continuous peripheral lips portion, wherein said lips portion is substantially elliptical and adapted to cover without extending significantly beyond the wearer's lips; and wherein said lips portion is flexible and resilient.

2. The oral prophylactic according to claim 1 further comprising non-toxic flavoring means selected from the group consisting of natural plant and fruit flavors, and synthetic compounds approximating natural plant and fruit flavors.

3. The oral prophylactic according to claim 1 further comprising texture means selected from the group consisting of ribs, dimples, setae, and striation grids.

4. An oral prophylactic for use in the mouth and adapted for the lips of a wearer comprising:
    an elastic unitary, liquid impermeable body having a thin-walled tubular portion received into the mouth over the tongue of the wearer, the tubular portion being closed at a first end located in the mouth of the wearer, and having an open end remote from said first end, said open end entirely surrounded by a continuous peripheral lips portion, wherein said lips portion is substantially elliptical and adapted to cover without extending significantly beyond the wearer's lips; and wherein said lips portion includes attachment means selected from the group consisting of an inner surface having an endless band of adhesive and integrally formed peripheral adhesive tabs.

5. The oral prophylactic according to claim 4 further comprising non-toxic lubrication and coloring means.

6. An oral prophylactic for use in the mouth and adapted for the lips of a wearer comprising:
    an elastic flexible, resilient body having a tubular portion received into the mouth above the tongue of the wearer, the tubular portion being closed at a first end located in the mouth of the wearer, and having an open end remote from said first end, said open end entirely surrounded by a continuous peripheral lips portion, wherein said lips portion is substantially elliptical and adapted to cover without extending significantly beyond the wearer's lips; and including a pocket extending into said first end for snugly receiving the tongue of the wearer.

7. The oral prophylactic according to claim 6 further comprising texture means selected from the group consisting of ribs, dimples, setae, and striation grids.

8. An oral prophylactic for use in the mouth and adapted for the lips of a wearer comprising:
    an elastic flexible, resilient body having a tubular portion received into the mouth above the tongue of the wearer, the tubular portion being closed at a first end located in the mouth of the wearer, and having an open end remote from said first end, said open end entirely surrounded by a continuous peripheral lips portion, wherein said lips portion is substantially elliptical and adapted to cover without extending significantly beyond the wearer's lips; and wherein at least part of the construction material is selected from the group consisting of porous membranes and silicone elastomers; and having non-toxic flavoring means selected from the group consisting of natural plant and fruit flavors, and synthetic compounds approximating natural plant and fruit flavors.

9. The oral prophylactic according to claim 8 further comprising non-toxic lubrication and coloring means.

* * * * *